United States Patent
Xu et al.

(10) Patent No.: US 9,593,344 B2
(45) Date of Patent: Mar. 14, 2017

(54) ENHANCED TRIACYLGLYCEROL ACCUMULATION IN VEGETATIVE TISSUES OF PLANTS

(71) Applicant: Brookhaven Science Associates, LLC, Upton, NY (US)

(72) Inventors: Changcheng Xu, Calverton, NY (US); Jilian Fan, Calverton, NY (US); Chengshi Yan, Coppell, TX (US); John Shanklin, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/790,139

(22) Filed: Jul. 2, 2015

(65) Prior Publication Data
US 2016/0002651 A1  Jan. 7, 2016

Related U.S. Application Data

(60) Provisional application No. 62/020,640, filed on Jul. 3, 2014.

(51) Int. Cl.
C12N 15/82 (2006.01)
C12N 5/14 (2006.01)

(52) U.S. Cl.
CPC ..... *C12N 15/8247* (2013.01); *C12N 15/8218* (2013.01); *C12N 5/14* (2013.01)

(58) Field of Classification Search
None
See application file for complete search history.

(56) References Cited

U.S. PATENT DOCUMENTS

| 7,626,079 B2 | 12/2009 | Baker et al. |
| 8,093,452 B2 | 1/2012 | Eastmond |
| 2013/0164798 A1* | 6/2013 | Vanhercke ............... C10L 1/04 435/134 |

OTHER PUBLICATIONS

Kelly et al 2013 (Plant Physiology 162:3, p. 1282-1289).*
Xu et al 2005 (Plant Cell 17: p. 3094-3110).*
Adeyo, O., et al., "The yeast lipin orthologue Pah1p is important for biogenesis of lipid droplets", (2011) J. Cell Biol. 192(6), pp. 1043-1055.
Alonso, J.M., "Genome-wide insertional mutagenesis of Arabidopsis thaliana", (2003) Science 301, pp. 1849-1849.
Bagnato, C. et al., "Overexpression of Diacylglycerol Acyltransferase-1 Reduces Phospholipid Synthesis, Proliferation, and Invasiveness in Simian Virus 40-transformed Human Lung Fibroblasts", (2003) J. Biol. Chem. 278, pp. 52203-52211.
Bao, X., et al., "Understanding in vivo carbon precursor supply for fatty acid synthesis in leaf tissue", (2000) Plant J. 22, pp. 39-50.
Bonaventure, G., et al., "Metabolic Responses to the Reduction in Palmitate Caused by Disruption of the FATB Gene in Arabidopsis", (2004) Plant Physiol. 135, pp. 1269-1279.
Browse, J., et al., "A Mutant of Arabidopsis Deficient in the Chloroplast 16:1/18:1 Desaturase", (1989) Plant Physiol. 30, pp. 522-529.
Caviglia, J.M., et al., "Phosphatidylcholine deficiency upregulates enzymes of triacylglycerol metabolism in CHO cells", (2004) J. Lipid Res. 45, pp. 1500-1509.
Chapman, K.D., et al., "Compartmentation of triacylglycerol accumulation in plants", (2012) J. Biol. Chem. 287, pp. 2288-2294.
Clough, S.J., et al., "Floral dip: a simplified method for Agrobacterium-mediated transformation of Arabidopsis thaliana", (1998) The Plant J. 16, pp. 735-743.
De Marcos Lousa, C., et al., "Intrinsic acyl-CoA thioesterase activity of a peroxisomal ATP binding cassette transporter is required for transport and metabolism of fatty acids", (2013) Proc. Natl. Acad. Sci. USA 110, pp. 1279-1284.
Dörmann, P., et al., "Isolation and characterization of an Arabidopsis mutant deficient in the thylakoid lipid digalactosyl diacylglycerol", (1995) The Plant Cell 7, pp. 1801-1810.
Eastmond, P.J., "Sugar-Dependent1 Encodes a Patatin Domain Triacylglycerol Lipase That Initiates Storage Oil Breakdown in Germinating Arabidopsis Seeds", (2006) The Plant Cell 18, pp. 665-675.
Eastmond, P.J., et al., "Phosphatidic acid phosphohydrolase 1 and 2 regulate phospholipid synthesis at the endoplasmic reticulum in Arabidopsis", (2010) The Plant Cell 22, pp. 4216-4216.
Fakas, S., et al., "Phosphatidate Phosphatase Activity Plays Key Role in Protection against Fatty Acid-induced Toxicity in Yeast", (2011) J. Biol. Chem. 286, pp. 29074-29085.
Fan, J., et al., "A chloroplast pathway for the de novo biosynthesis of triacylglycerol in Chlamydomonas reinhardtii", (2011) FEBS Lett. 585, pp. 1985-1991.
Fan, J.L., et al., "Phospholipid:diacylglycerol acyltransferase-mediated triacylglycerol biosynthesis is crucial for protection against fatty acid-induced cell death in growing tissues of Arabidopsis", (2013) The Plant J. 76:930-942.
Fan, J.L., et al., "Arabidopsis Lipins, PDAT1 Acyltransferase, and SDP1 Triacylglycerol Lipase Synergistically Direct fatty Acids toward β-Oxidation, Thereby Maintaining Membrane Lipid Homeostasis", (2013) The Plant Cell 25:3506-3518.
Gaspar, M.L., et al., "A block in endoplasmic reticulum-to-Golgi trafficking inhibits phospholipid synthesis and induces neutral lipid accumulation", (2008) J. Biol. Chem. 283:25735-25751.
Ghosh, A.K., et al., "At4g24160, a soluble acyl-coenzyme A-dependent lysophosphatidic acid acyltransferase", (2009) Plant Physiol. 151:869-881.
Golden, A., et al., "Inactivation of the C. elegans lipin homolog leads to ER disorganization and to defects in the breakdown and reassembly of the nuclear envelope", (2009) J. Cell Sci. 122:1970-1978.

(Continued)

*Primary Examiner* — Matthew Keogh
(74) *Attorney, Agent, or Firm* — Dorene M. Price (57) ABSTRACT

In the tgd1-1 mutant that displays substantially enhanced TAG synthesis and turnover, disruption of SUGAR-DEPENDENT1 (SDP1) TAG lipase or PEROXISOMAL TRANSPORTER1 (PXA1) severely decreases FA turnover, leading to an increase in leaf TAG content up to 9% of dry weight and total leaf lipid by three-fold. The membrane lipid content and composition of tgd1-1 sdp1-4 and tgd1-1 pxa1-2 double mutants are altered and they are compromised in growth and development and fertility.

16 Claims, 3 Drawing Sheets

(56) References Cited

OTHER PUBLICATIONS

Graham, I.A., "Seed storage oil mobilization", (2008) Ann. Rev. Plant Biol. 59:115-142.
Hajdukiewicz, P., et al., "The small, versatile pPZP family of Agrobacterium binary vectors for plant transformation", (1994) Plant Mol. Biol. 25:989-994.
Härtel, H., et al., "DGD1-independent biosynthesis of extraplastidic galactolipids after phosphate deprivation in Arabidopsis", (2000) Proc. Natl. Acad. Sci. USA 97:10649-10654.
Henry, S.A., et al., "Metabolism and regulation of glycerolipids in the yeast *Saccharomyces cerevisiae*", (2012) Genetics 190:317-349.
Hermansson, M., et al., "Mechanisms of glycerophospholipid homeostasis in mammalian cells", (2011) Prog. Lipid Res. 50:240-257.
Holthuis, J.C., et al., "Lipid landscapes and pipelines in membrane homeostasis", (2014) Nature 510:48-57.
Igal, R.A., et al., "Acylglycerol Recycling from Triacylglycerol to Phospholipid, Not Lipase Activity, Is Defective in Neutral Lipid Storage Disease Fibroblasts", (1996) J. Biol. Chem. 271:16644-16651.
James, C.N., et al., "Disruption of the Arabidopsis CGI-58 homologue produces Chanarin-Dorfman-like lipid droplet accumulation in plants", (2010) Proc. Natl. Acad. Sci. USA 107:17833-17838.
Kelly, A.A., et al., "Seed storage oil mobilization is important but not essential for germination or seedling establishment in Arabidopsis", (2011) Plant Physiol. 157:866-875.
Kelly, A.A., et al., "The Sugar-Dependent1 Lipase Limits Triacylglycerol Accumulation in Vegetative Tissues of Arabidopsis", (2013) Plant Physiol. 162:1282-1289.
Kobayashi, K., et al., "Galactolipid synthesis in chloroplast inner envelope is essential for proper thylakoid biogenesis, photosynthesis, and embryogenesis", (2007) Proc. Natl. Acad. Sci. USA 104:17216-17221.
Kohlwein, S.D., et al., "Lipid droplets and peroxisomes: key players in cellular lipid homeostasis or a matter of fat—store 'em up or burn 'em down", (2013) Genetics 193:1-50.
Koo, A.J.K., et al., "Identification of a plastid acyl-acyl carrier protein synthetase in Arabidopsis and its role in the activation and elongation of exogenous fatty acids", (2005) The Plant J. 44:620-632.
Kunst, L., et al., "Altered regulation of lipid biosynthesis in a mutant of Arabidopsis deficient in chloroplast glycerol-3-phosphate acyltransferase activity", (1988) Proc. Natl. Acad. Sci. USA 85:4143-4147.

Kunz, H.H., et al., "The ABC transporter PXA1 and peroxisomal beta-oxidation are vital for metabolism in mature leaves of Arabidopsis during extended darkness", (2009) The Plant Cell 21:2733-2749.
Leonardi, R., et al., "Elimination of the CDP-ethanolamine pathway disrupts hepatic lipid homeostasis", (2009) J. Biol. Chem. 284:27077-27089.
Malanovic, N., et al., "S-adenosyl-L-homocysteine hydrolase, key enzyme of methylation metabolism, regulates phosphatidylcholine synthesis and triacylglycerol homeostasis in yeast: implications for homocysteine as a risk factor of atherosclerosis", (2008) J. Biol. Chem. 283:23989-23999.
Murashige, T., et al., "A Revised Medium for Rapid Growth and Bio Assays with Tobacco Tissue Cultures", (1962) Physiol. Plant 15:473-497.
Nakamura, Y., et al., "Arabidopsis lipins mediate eukaryotic pathway of lipid metabolism and cope critically with phosphate starvation", (2009) Proc. Natl. Acad. Sci. USA 106:20978-20983.
Nohturfft, A., et al., "Coordination of lipid metabolism in membrane biogenesis", (2009) Ann. Rev. Cell Dev. Biol. 25:539-566.
Ohlrogge, J., et al., "Lipid biosynthesis", (1995) The Plant Cell 7:957-970.
Park, S., et al., "The α/β Hydrolase CGI-58 and Peroxisomal Transport Protein PXA1 Coregulate Lipid Homeostasis and Signaling in Arabidopsis", (2013) The Plant Cell 25:1726-1739.
Petschnigg, J., et al., "Good Fat, Essential Cellular Requirements for Triacylglycerol Synthesis to Maintain Membrane Homeostasis in Yeast", (2009) J. Biol. Chem. 284:30981-30993.
Santos-Rosa, H., et al., "The yeast lipin Smp2 couples phospholipid biosynthesis to nuclear membrane growth", (2005) EMBO J. 24:1931-1941.
Slocombe, S.P., et al., "Oil accumulation in leaves directed by modification of fatty acid breakdown and lipid synthesis pathways" (2009) Plant Biotechnology J. 7:694-703.
Theodoulou, F.L., et al., "Seed storage oil catabolism: a story of give and take", (2012) Curr. Opin. in Plant Biol. 15:322-328.
van Meer, et al., "Membrane lipids: where they are and how they behave", (2008) Nat. Rev. Mol. Cell Biol. 9:112-124.
Xu, C., et al., "Lipid Trafficking between the Endoplasmic Reticulum and the Plastid in Arabidopsis Requires the Extraplastidic TGD4 Protein", (2008) The Plant Cell 20:2190-2204.
Xu, C., et al., "A permease-like protein involved in ER to thylakoid lipid transfer in Arabidopsis", (2003) EMBO J 22:2370-2379.
Xu, C., et al., "Mutation of the TGD1 chloroplast envelope protein affects phosphatidate metabolism in Arabidopsis", (2005) The Plant Cell 17:3094-3110.

\* cited by examiner

ENHANCED TRIACYLGLYCEROL ACCUMULATION IN VEGETATIVE TISSUES OF PLANTS

PARENT CASE

This application claims the benefit of U.S. Provisional Application 62/020,640 filed on Jul. 3, 2014, the entire contents of which are incorporated herein by reference.

GOVERNMENT SUPPORT

This invention was made with Government support under contract number DE-AC02-98CH10886 and DE-SC0012704, awarded by the U.S. Department of Energy. The Government has certain rights in the invention.

BACKGROUND

Plant oils in the form of triacylglycerols (TAGs) have twice the energy content of carbohydrates and proteins. Therefore, increasing oil accumulation in vegetative tissues would enhance the energy density and nutritional value of biomass, and could have a major positive impact on the use of biomass as feed and for the production of biofuel and bioelectricity. In addition, using abundant vegetative biomass as vessels of oil accumulation increases the oil storage capacity of plants and has the potential to provide abundant supplies of plant oils for biodiesel production without diverting land from other uses, and thus avoiding a competition between food and biofuel.

Despite the fact that most plant cells have a high capacity to synthesize TAGs, plant vegetative tissues do not accumulate oil to a significant amount. This is because 1) TAGs undergo rapid turnover in plant vegetative tissues; 2) fatty acids, the predominant components of TAG, are used for membrane construction which limits their availability for accumulation in TAGs. Therefore, blocking TAG turnover and increasing fatty acid synthesis represent two key facets of genetic engineering efforts aimed at enhancing TAG accumulation in vegetative tissues of plants.

Previous attempts to enhance fatty acid synthesis mostly focus on transcriptional regulators such as WRINKLED1 (WRI1) that is known to be involved in the activation of fatty acid synthesis genes in oilseeds. However, overexpression of seed-specific transcription factors in vegetative tissues often leads to adverse growth and developmental defects. In addition, overexpression of WRI1 alone does not increase fatty acid synthesis and therefore has had limited positive impact on oil content in plant vegetative tissues.

Prior approaches to blocking TAG turnover include 1) disruption of the peroxisomal transporter1 (PXA1) or sugar-dependent1 TAG lipase responsible for the initiation of TAG breakdown; and 2) Overexpression of seed-specific oil droplet-associated proteins, oleosins, which coat oil droplets (ODs), the TAG storage compartments, thereby blocking oil breakdown by preventing the access of TAG lipases to oil droplets.

We recently reported that overexpression of phospholipid: diacylglycerol acyltransferase1 (PDAT1) boosts both fatty acid and TAG synthesis in leaves. The combined expression of PDAT1 and oleosin1 increased leaf TAG content to 8.6% on a dry weight basis. Several other groups reported that overexpression of WRI1 in combination with diacylglycerol acyltransferase1 (DGAT1) and oleosin results in increased oil production in plant vegetative tissues.

Recently, Kelly et al. (2013) have demonstrated that over expression of WRI and DGAT1 in a sugar-dependent1 lipase-deficient mutant line (sdp1) stimulated TAG accumulation in leaves, stems and roots whereas the sdp1 mutant line accumulated enhanced levels of TAG only in roots and in stems.

According to recent analyses, if 10% of the harvested dry material from high yield biomass crops such as *Miscanthus* is oil, the oil yield per hectare of such an energy crop would surpass oilseed rape by more than 2-fold. Thus, applying genetic engineering approaches to dedicated bioenergy crops could greatly enhance the nutritional value of vegetative tissues and have the potential to greatly expand the production of plant oils as sustainable sources of biodiesel and industrial chemicals.

BRIEF DESCRIPTION

Herein disclosed are plants with enhanced TAG in vegetative tissues, particularly in leaves, that are generated by combined disruption of the TAG breakdown pathway and chloroplast lipid import machinery. Specifically, mutations in a gene encoding a protein named TGD1 (trigalactosyldiacylglycerol1), causes a defect in the import of lipid molecules into chloroplasts from the endoplasmic reticulum, and results in an up to 4-fold increase in the rates of both fatty acid (FA) synthesis and breakdown. Blocking FA turnover by knockout of either sugar-dependent1 triacylglycerol lipase (SDP1) or peroxisomal transporter1 (PXA1) in a mutant defective in TGD1, tgd1-1, increased leaf TAG content to about 9% per dry weight at 7 weeks after sowing, corresponding to an average rate of TAG increase of 1.3% per dry weight per week. If a similar rate of TAG accumulation could be achieved in crop plants, a much higher TAG level may conceivably be reached by leaf maturation, since many crops have much longer life cycles than *Arabidopsis*, the plant species used for the examples included herein. For example, the growth period of a tobacco leaf may extend to 30 weeks under natural growth conditions. Thus, the calculated oil content in mature tobacco leaves could be as high as 39% (30×1.3%) per dry weight, an oil level equivalent to that of canola seeds. Further increases in the rate of TAG accumulation in the tgd1-1 sdp1 or tgd1-1 pxa1 background may still be possible by overexpression of WRI1 and/or by overexpression of PDAT1 and oleosins.

DETAILED DESCRIPTION

Trigalactosyldiacylglycerol (TGD) proteins are a group of proteins required for lipid import into chloroplasts from endoplasmic reticulum. The TGD proteins TGD1, TGD2, and TGD3 form a multipartite ABC lipid transporter. The work of Xu, et al. (2003 and 2005) describe the identification and effects of mutation of the TGD1 protein and the generation of the mutant lines, including tgd1-1 cells and plants.

While mutant cells and mutant plants bearing the tgd1-1 mutation in combination with knockout of either sugar dependent1 lipase (SDP1) or peroxisomal transporter1 (PXA1) are exemplified herein, cells and plants bearing other inactivated TGD proteins and mutated TGD genes and alleles or other inactive alleles of TGD1 in combination with inactivated or otherwise suppressed lipase and transporter activities produced by methods other than by knockout are expected to also result in plant vegetative tissues having enhanced dry weight percentage TAG.

Enhanced dry weight percentage TAG in vegetative tissue is any percentage that is substantially above the amount present in normal vegetative tissue of the same age or maturation stage. Contemplated herein are plant tissues having 5% or more dry weight percentage TAG.

Inactivation of the proteins involved in enhancing TAG accumulation in vegetative tissue (i.e., inactivation of the TGD, the SDP1 and/or the PXA1 proteins) may be accomplished by means known in the art. Establishing cell and plant lines comprising inactive proteins is most readily achieved by mutagenesis of the genes encoding the targeted protein.

Mutagenesis, as used herein, refers to the process in which plant cells (e.g., a plurality of plants seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more TGD encoding alleles or the SDP1 or PXA1 genes may be accomplished by use of chemical means such as by treatment of one or more plant cells, tissues, or seeds, with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, plants can be regenerated from the treated cells using known techniques or treated seeds may be planted in accordance with conventional growing procedures.

Alternatively the genes encoding the TGD, SDP1 or PXA1 proteins may be disrupted by insertion and other deletion, e.g., by knockout or knockdown.

The mutagenesis and knockout/down methods result in producing a defective gene encoding the protein.

Alternatively the expression of the genes encoding the TGD, SDP1 or PXA1 proteins can be suppressed, for example by transformation of the cells with inhibitory RNA. Inhibitory RNA as herein used includes antisense RNA, co-suppression (sense) RNA, double stranded RNA including hairpinRNA, siRNA, microRNA and precursors thereof.

Plants and plant cells having an inactive, defective or suppressed TGD1 protein and/or the SDP1 or PXA1 protein activities are plants and cells having less than about 50% of the normal, wild type levels, of the activity of the proteins. A plant or cell having less than about 70% of normal wild type activity is preferred and a plant or cell having less than about 90% of normal activity is even more preferable.

DETAILED BACKGROUND AND RESULTS

Intracellular lipid homeostasis is vital for normal membrane structure and functions and for cell survival in response to lipid metabolism perturbations that result from environmental stresses or other causes (van Meer et al., (2008); Hermansson et al., 2011; Holthuis and Menon, 2014). Although most of the enzymatic steps in lipid biosynthetic pathways are defined at the molecular-genetic level in several model organisms (Nohturfft and Zhang, 2009; Chapman and Ohlrogge, 2012; Henry et al., 2012), our understanding of how intracellular lipid homeostasis is maintained in plants remains rudimentary (Kunz et al., 2009; Fan et al., 2013a; Park et al., 2013)

Studies in yeast and mammals suggest that TAG synthesis, storage and mobilization are key aspects of intracellular lipid homeostasis and energy balance. Under conditions of acute lipid overload, excess lipids are converted into biologically inert TAG and packaged in specific subcellular organelles named oil droplets (ODs) (Listenberger et al., 2003; Petschnigg et al., 2009; Kohlwein et al., 2013). In yeast, a critical enzyme involving in TAG synthesis (Han et al., 2006, 2007) and oil droplet formation (Adeyo et al., 2011) is the $Mg^{2+}$-dependent phosphatidic acid phosphohydrolases (Pah1), a homolog of the mammalian lipin protein family. Yeast mutant cells lacking Pah1 display elevated phospholipid levels (Han et al., 2006, 2007), a massive proliferation of endoplasmic reticulum (ER) and nuclear membranes (Santos-Rosa et al., 2005), and increased sensitivity to exogenous FA-induced cell death (Fakas et al., 2011). Similarly, inactivation of the C. elegans lipin homolog has been shown to cause decreased fat storage and altered ER membrane structure (Golden et al., 2009). Arabidopsis lipins, PAH1 and PAH2, have been implicated in the synthesis of thylakoid membrane lipids (Kobayashi et al., 2007) and in the regulation of phospholipid synthesis and ER membrane organization, but surprisingly disruption of the Arabidopsis lipins causes only a small reduction in seed oil content (Eastmond et al., 2010). The role of Arabidopsis lipins in TAG biosynthesis in vegetative tissues is currently unknown.

Likewise, disruption of membrane phospholipid synthesis in mammalian cells (Caviglia et al., 2004; Leonardi et al., 2009) or yeast (Malanovic et al., 2008), or a block in intracellular lipid trafficking in yeast (Gaspar et al., 2008) or plants (Xu et al., 2005; Xu et al., 2008) increases lipid flux to TAG synthesis and storage. In contrast, increasing TAG synthesis by overexpression of acyl-CoA:diacylglycerol acyltransferase1 (DGAT1) has been shown to cause a decrease in membrane phospholipid content in human cells (Bagnato and Igal, 2003). Interplay between TAG metabolism and membrane lipid synthesis is demonstrated by studies showing that storage TAG hydrolysis can function as a source of lipid precursors for the synthesis of membrane phospholipids and signaling lipids in both yeast and mammals (Igal and Coleman, 1996; Kohlwein et al., 2013). Deficits in acylglycerol recycling from TAG to phospholipids are the likely cause of a neutral lipid storage disease in humans caused by mutations in COMPARATIVE GENE IDENTIFIER58 (CGI58) (Igal and Coleman, 1996). Disruption of the *Arabidopsis* CGI58-LIKE (CGI58L) results in increased TAG accumulation, decreased jasmonate production and altered responses to auxin, implying a role for CGI58L in lipid turnover and signaling (James et al., 2010; Park et al., 2013).

In oilseeds, TAG serves as a major fatty acid (FA) source for energy production and gluconeogenesis during germination and seedling establishment (Graham, 2008; Theodoulou and Eastmond, 2012). TAG catabolism begins with the release of its fatty acyl chains by the action of an evolutionally-conserved family of patatin domain-containing enzymes (Eastmond, 2006). There are several patatin-like TAG lipase candidates in *Arabidopsis* including SUGAR-DEPENDENT1 (SDP1), SUGAR-DEPENDENT1-LIKE (SDP1L) and ADIPOSE TRIGLYCERIDE LIPASE-LIKE (ATGLL) (Eastmond, 2006). In plants and yeast, the major pathway for metabolic breakdown of FAs is β-oxidation in peroxisomes (Graham, 2008; Theodoulou and Eastmond, 2012) and FAs in the form of their CoA esters are transported into this organelle by PEROXISOMAL TRANSPORTER1 (PXA1) (De Marcos Lousa et al., 2013). Recent genetic studies have implicated PXA1, SDP1 and SDP1L in TAG breakdown in non-seed tissues (Slocombe et al., 2009; Kelly et al., 2013), but the physiological function of TAG turnover and the regulatory aspects of FA β-oxidation pathway in leaves remain largely unknown.

In addition to TAG metabolism, biochemical and genetic studies have shown that changes in the balance between different glycerolipid pathways contribute to the maintenance of membrane lipid homeostasis. In photosynthetic tissues, two galactolipids, monogalactosyldiacylglycerol (MGDG) and digalactosyldiacylglycerol (DGDG), constitute the bulk of cellular membrane lipids and their synthesis in *Arabidopsis* involves two distinct pathways, namely the prokaryotic and eukaryotic pathways (Ohlrogge and Browse, 1995). Inactivation of either pathway can be offset by upregulation of the other so that the overall membrane lipid content and composition remains largely unchanged. This is best exemplified by the plastidic glycerol-3-phosphate acyltransferase1 (act1) (Kunst et al., 1988) and the trigalactosyldiacylglycerol1-1 (tgd1-1) (Xu et al., 2003) mutants, which are defective in the prokaryotic or eukaryotic pathway of thylakoid lipid synthesis, respectively. Likewise, diversion of FAs from the eukaryotic thylakoid lipid synthesis to TAG synthesis upon the overexpression of phospholipid:diacylglycerol acyltransferase1 (PDAT1) is accompanied by an increase in FA toward prokaryotic lipid synthesis without affecting the membrane lipid content (Fan et al., 2013b). Although the exact mechanism underlying this homeostasis remains unclear, we recently identified a compensating mechanism in which FA synthesis is increased in both the tgd1-1 mutant and PDAT1 overexpressing lines (Fan et al., 2013a; Fan et al., 2013b). In addition, the FA turnover rate is markedly enhanced in leaves of the tgd1-1 mutant. An unexpected finding here is that two *Arabidopsis* lipins, PDAT1 and SDP1, function synergistically in regulating FA flow from membrane lipid synthesis toward peroxisomal β-oxidation through a transient TAG pool, and that blocking FA turnover alters membrane lipid content and composition in addition to compromising plant growth and development in the tgd1-1 mutant.

Overexpression of PDAT1 Enhances Both the Synthesis and Turnover of FAs:

Overexpression of PDAT1 enhances both FA and TAG synthesis in leaves (Fan et al., 2013b). In rosette leaves of the three independent transgenic lines, the rates of FA synthesis measured as the rate of $^{14}C$-acetate incorporation into total FAs were 61% to 82% higher in leaves of 5-week-old transgenic lines overexpressing PDAT1 relative to the wild type. Since the overall membrane lipid content remained largely unaltered, the increased rates of FA synthesis must result from corresponding increases in rates of FA turnover. To test this hypothesis, detached leaves were labeled with $^{14}C$-acetate for 1 h, and the changes in the concentration of labeled FAs were then chased for 3 days. In the wild type, the decline in labeled FAs during the 3 day chase period was 13%. This corresponds to a FA turnover rate of 4.3% per day, a value that is similar to that previously measured in wild-type *Arabidopsis* plants based on an isotope dilution method (Bao et al., 2000), but higher than that reported by Bonaventure et al. (2004). By comparison, the average decay rate of labeled FAs was increased to 6.7% per day in PDAT1 overexpressing lines. These results suggest that overexpression of PDAT1 enhances the rates of both synthesis and degradation of FAs in leaves.

FA Turnover Involves SDP1 and PXA1:

Recent genetic studies have implicated SDP1 in TAG breakdown in vegetative tissues of *Arabidopsis* (Kelly et al., 2013). To determine the role of SDP1 in FA turnover in leaves of transgenic plants overexpressing PDAT1, genetic crosses were made between the PDAT1 overexpressing line 3 and sdp1-4 (Eastmond, 2006), and plants carrying the PDAT1 transgene in the sdp1-4 genetic background were subsequently identified. Leaf TAG levels (per DW) almost doubled in the PDAT1 overexpressing line 3 in the sdp1-4 genetic background (1.12±0.22% per DW, n=3) compared with the PDAT1 overexpressing line 3 in the wild-type background (0.57±0.13% per dry weight (DW, n=3). These results imply that TAG turnover in PDAT1 overexpressing lines involves SDP1.

Besides SDP1, the *Arabidopsis* genome contains at least two additional putative patatin-like TAG lipases, namely SDP1L and ATGLL (Eastmond, 2006). *Arabidopsis* CGI58L, a member of the α/β hydrolase family of proteins, has been shown to exhibit TAG lipase activity in addition to lysophosphatidic acid acyltransferase activity (Ghosh et al., 2009). To systematically test the in vivo functions of these candidate TAG lipases in leaf FA turnover, we performed double mutant analyses taking advantage of the previously described tgd1-1 mutant line that accumulates TAG in leaves (Fan et al., 2013a), and the mutants with T-DNA insertions in SDP1 (sdp1-4, Eastmond, 2006), SDP1L (sdp1L-2, Kelly et al., 2011), CGI58L (cgi58L, James et al., 2010) or ATGL (atgL, Kelly et al., 2011) genes. We additionally generated a double mutant of tgd1-1 and a knockout mutant pxa1-2 (Kunz et al., 2009) that contains a T-DNA insertion in the PXA1 gene to test whether TAG turnover in tgd1-1 lines is mediated by β-oxidation in peroxisomes.

Figure 1:
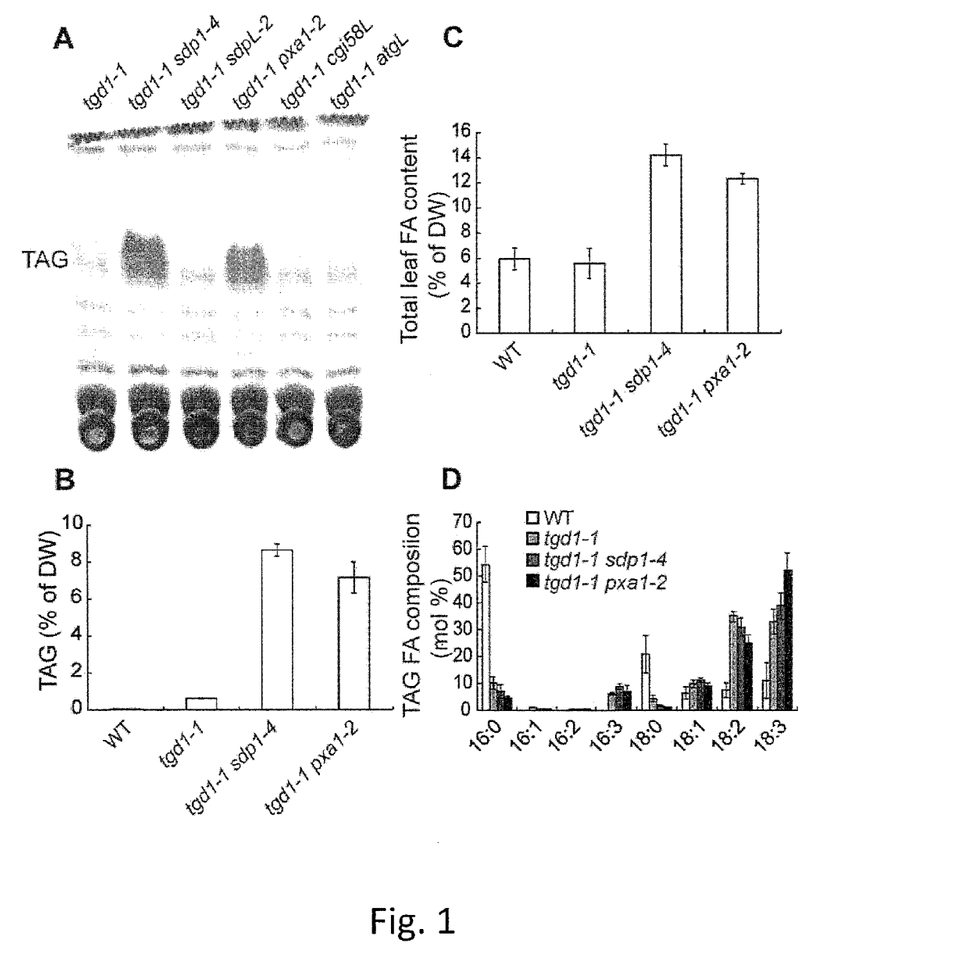
FIG. 1: Boosting leaf TAG accumulation in tgd1-1. (A) Thin layer chromatogram of neutral lipids. (B) TAG content in leaves of 7-week-old plants grown on soil. (C) and (D) Total FA content (C) and TAG FA composition (D) in leaves of wild-type (WT) and mutant plants. Values in B, C and D are means and standard deviation of three replicates.

Compared with the tgd1-1 single mutant, no obvious differences in leaf TAG content were found in tgd1-1 lacking SDP1L, CGI58L or ATGL expression (FIG. 1A). In contrast, disruption of SDP1 or PXA1 led to a marked increase in leaf TAG accumulation in tgd1-1. On a DW basis, the amounts of TAG in leaves of 7-week-old plants grown on soil increased from 0.6% in tgd1-1 to 8.8% and 8.1% in tgd1-1 sdp1-4 and tgd1-1 pxa1-2, respectively (FIG. 1B). The increased TAG level in tgd1-1 sdp1-4 and tgd1-1 pxa1-2 was accompanied by a corresponding rise in total leaf FA content to 14.2 and 12.3% per DW, respectively (FIG. 1C), suggesting that TAG accumulation is a result of decreased hydrolysis rather than a mere redistribution of FAs from membrane lipids to TAG. FA compositional analysis showed that the predominant FAs in TAG derived from the leaves of both tgd1-1 sdp1-4 and tgd1-1 pxa1-2 are polyunsaturated FAs, with 18:2 and 18:3 accounting for over 70% of the total TAG acyl chains (FIG. 1D). The FA composition of TAG from leaves of tgd1-1 sdp1-4 was similar to that of tgd1-1 except for a small increase in the relative proportion of 16:3 at the expense of 18:0 in the double mutant. In TAG from leaves of tgd1-1 pxa1-2, there was a marked increase in 18:3, balanced by a decrease in saturated FAs and 18:2 (FIG. 1D).

Figure 2:
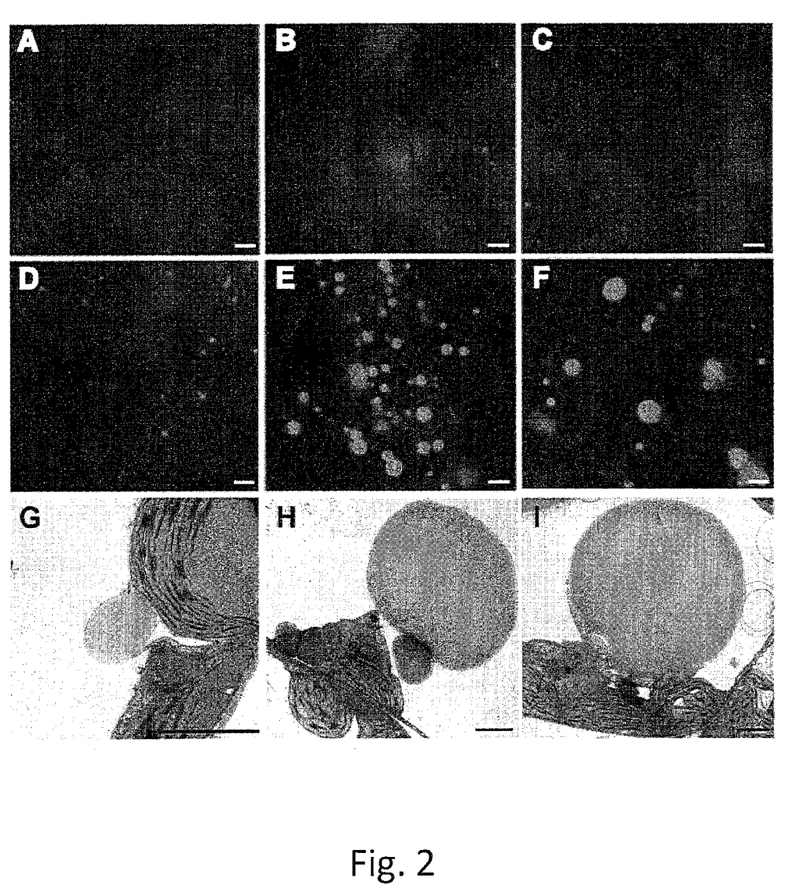
FIG. 2: Oil Droplet (OD) accumulation in leaves. (A) to (F) Fluorescence images of ODs in wild-type (A), sdp1-4 (B), pxa1-2 (C), tgd1-1 (D) tgd1-1 sdp1-4 (E) and tgd1-1 pxa1-2 (F) (leaves stained with Nile red. Bars=10 µm.) (G) to (I) TEM images of leaf cells of tgd1-1 (G) tgd1-1 sdp1-4 (H) and tgd1-1 pxa1-2 (I). Bars=2 µm.

Fluorescence microscopy examination following Nile Red staining revealed no or only a few small OD-like structures in leaves of the wild type, sdp1-4, pxa1-2, and small and few ODs in the tgd1-1 single mutants (FIGS. 2 A, B, C and D). Leaves of tgd1-1 sdp1-4 and tgd1-1 pxa1-2 double mutants (FIGS. 2 E and F), on the other hand, showed marked increases in both the size and number of oil droplets (ODs) compared with wild type and single mutant leaves. Ultrastructural imaging using transmission electron microscopy (TEM) confirmed the presence of ODs larger than 10 μm in diameter in leaf mesophyll cells of the tgd1-1 sdp1-4 and tgd1-1 pxa1-2 double mutants (FIGS. 2 H and I).

The amounts of TAG appeared to increase slightly in leaves of the single mutant disrupted in SDP1 or PXA1 compared with the wild type, whereas no obvious difference in leaf TAG content was found in the single mutant carrying T-DNA insertion in the SDP1L, CGI58L or ATGL gene. The lack of effect of CGI58L disruption on TAG content under our growth conditions may reflect the dynamic nature of OD accumulation in cgi58L, being apparent only at certain stages of leaf development (James et al., 2010).

Disruption of SDP1 or PXA1 Affects Plant Growth and Development in tgd1-1:

Homozygous single mutants of both sdp1-4 and pxa1-2 displayed growth and developmental patterns similar to the wild type. The tgd1-1 sdp1-4 and tgd1-1 pxa1-2 double mutants, on the other hand, were stunted in both aerial parts of seedlings and roots, particularly the tgd1-1 pxa1-2 double mutant compared with tgd1-1, when grown on agar-solidified Murashige and Skoog (MS) plates supplemented with 1% sucrose. The growth defects also extended to plants grown on soil, but the final plant size and height were similar between tgd1-1 and the double mutants.

The bolting time was slightly delayed in both tgd1-1 sdp1-4 and tgd1-1 pxa1-2 compared with tgd1-1. While the seed setting appeared to be normal in tgd1-1 sdp1-4, the tgd1-1 pxa1-2 plants were completely infertile. Cross-pollination of tgd1-1 pxa1-2 double mutant plants with tgd1-1 pollen resulted in seed production, but reciprocal crossing did not yield seeds, indicating a pollen defect in tgd1-1 pxa1-2. Close examination of the flowers revealed no obvious morphological differences between and tgd1-1 and tgd1-1 pxa1-2. Assaying pollen viability by Alexander staining indicated that the mature tgd1-1 pxa1-2 anthers contained abundant viable pollen grains. However, no or only a few pollen grains from freshly anther-dehisced flowers of the tgd1-1 pxa1-2 double mutant germinated in either in vitro or in vivo pollen germination assays. By contrast, most of pollen grains from tgd1-1 germinated and their pollen tubes elongated. These results suggest that disruption of PXA1 causes a defect in pollen germination in the tgd1-1 background.

Figure 3:
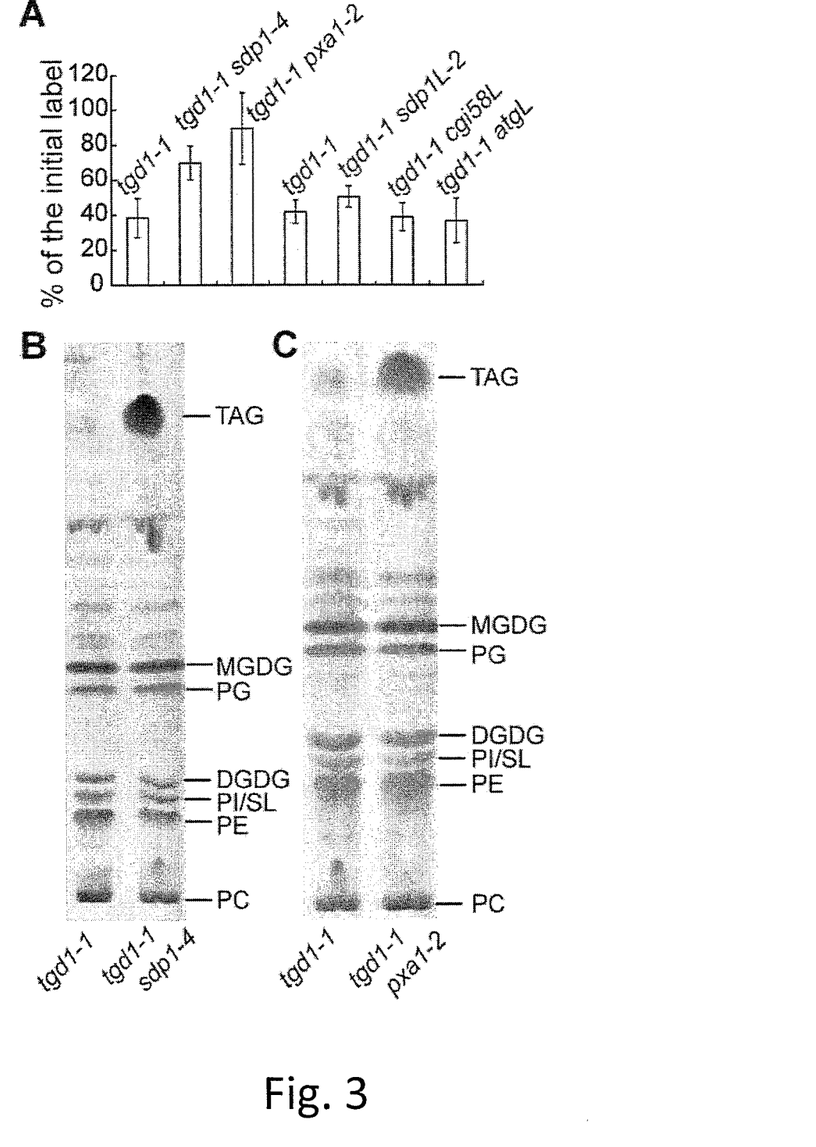
FIG. 3: Disruption of SDP1 or PXA1 enhances FA flux to TAG in tgd1-1. Detached leaves were labeled with $^{14}$C-acetate for 1 h, and then the label chased for 3 days (d). Values are means and standard deviation of three replicates. (A) Decreases in total labeled FAs during the chase period in tgd1-1 and double mutants. (B) and (C) Autoradiograph of radiolabeled lipids separated by TLC using a double development. Abbreviations: MGDG, monogalactosyldiacylglycerol; DGDG, digalactosyldiacylglycerol; PE, phosphatidylethanolamine; PG, phosphatidylglycerol; PI, phosphatidylinositol; PC, phosphatidylcholine; SL, sulfoquinovosyldiacylglycerol; TAG, triacylglycerol.

Disruption of SDP1 or PXA1 Blocks FA Turnover and Markedly Enhances FA Flux Toward TAG in the tgd1-1 Background:

To test whether FA turnover was affected in double mutants, we analyzed the decay rate of labeled FAs in pulse-chase experiments with $^{14}$C-acetate. The results showed that, knockout of SDP1 or PXA1 resulted in marked decreases in rates of labeled FA degradation in the tgd1-1 background, whereas no apparent differences were found between tgd1-1 and tgd1-1 sdp1-2, tgd1-1 atglL or tgd1-1 cgi58L (FIG. 3A). To determine whether the decreased rates of FA turnover were associated with specific lipids, we analyzed the radiolabel distribution in individual glycerolipids in tgd1-1, tgd1-1 sdp1-4 and tgd1-1 pxa1-2 following the 3 day chase period. This analysis revealed that disruption of SDP1 or PXA1 led to a marked increase in radiolabel in TAG in tgd1-1 sdp1-4 and tgd1-1 pxa1-2, whereas the radioactivity in major membrane lipid classes appeared to be largely unaltered in the double mutants compared with tgd1-1 (FIG. 3B). Accordingly, as much as 48.6%±1.4% and 35%±4.1% (n=3) of total labeled FAs were associated with TAG in tgd1-1 sdp1 and tgd1-1 pxa1-2, respectively, compared with only 9.6%±3.4% (n=3) of the labeled FAs in TAG in tgd1-1.

Previous studies have shown that SDP1 and SDP1L function redundantly in TAG hydrolysis in germinating seeds of *Arabidopsis* (Eastmond, 2006; Kelly et al., 2013). To test whether this is also the case in leaves, we constructed a triple mutant impaired in both SDP1 and SDP1L functions in the tgd1-1 mutant background. Quantification of leaf TAG content revealed no significant difference (P=0.22, n=3) between tgd1-1 sdp1-4 (8.2%±0.7% per DW) and tgd1-1 sdp1-4 sdp1l-2 (8.9±0.4% per DW). The lack of an effect of SDP1L knockout on leaf TAG content is perhaps not unexpected, since previous expression analysis showed that expression of SDP1L transcript is very low in leaves but high in pollen (Kelly et al., 2011).

Based on double mutant analysis, it has been shown that PXA1 is epistatic to SDP1 in regulating TAG content in roots (Kelly et al., 2013). To determine the genetic relationship between these two genes in TAG accumulation in leaves, we generated a triple mutant of tgd1-1 sdp1-4 pxa1-2. Compared with the tgd1-1 sdp1-4 and tgd1-1 pxa1-2, no apparent difference in leaf TAG content was found between the tgd1-1 sdp1-4 pxa1-2 triple mutant and tgd1-1 sdp1-4 or tgd1-1 pxa1-2. The FA composition of TAG in the triple mutant was also identical to that found in tgd1-1 pxa1-2. On soil, the tgd1-1 sdp1-4 pxa1-2 triple mutant showed similar growth and developmental patterns to tgd1-1 pxa1-2, and was completely infertile. Taken together, these results support the idea that SDP1 acts in the same pathway with PXA1 to affect TAG metabolism and plant growth and development.

Disruption of SDP1 or PXA1 Alters Membrane Lipid Content and FA Composition in the tgd1-1 Background:

To further assess the impact of blocked FA turnover on lipid metabolism, we analyzed the membrane lipid composition in leaves of single and double mutants. The levels of individual membrane lipids were identical among the wild type, sdp1-4 and pxa1-2. In addition, there was no obvious difference in FA composition of total leaf lipids between the wild type and the single mutants lacking SDP1 or PXA1.

In contrast, disruption of SDP1 or PXA1 alters both membrane lipid content and FA composition in the tgd1-1 mutant background. On a DW basis, the amounts of two major extraplastidic membrane phospholipids PC and PE were substantially increased in leaves of both tgd1-1 sdp1-4 and tgd1-1 pxa1-2. In addition, the levels of galactolipids MGDG and DGDG were significantly elevated in tgd1-1 sdp1-4, but not in tgd1-1 pxa1-2 compared with tgd1-1. As a consequence, the total amounts of membrane lipids increased by 35% and 12% in tgd1-1 sdp1-4 and tgd1-1 pxa1-2, respectively, relative to tgd1-1. Examining the FA composition of individual membrane lipids revealed a substantial increase in the proportion of 18:2 at the expense of 18:3 in both PC and PE in tgd1-1 sdp1-4. In tgd1-1 pxa1-2, there was an increase in 18:3 in PC and PE with a concomitant decrease in saturated acyl chains. The changes in the FA composition of major thylakoid lipids MGDG and DGDG appeared to be less pronounced in the double mutants compared with tgd1-1. However, there was a substantial increase in the relative level of 18:3 at the expense of 16-carbon (C16) FAs in galactolipids in both tgd1-1 sdp1-4 and tgd1-1 pxa1-2 relative to tgd1-1.

Since C16 FAs are predominantly associated with thylakoid lipids made by the prokaryotic pathway (Browse et al., 1989), the decreased C16 level may indicate a shift in the balance between two glycerolipid biosynthetic pathways. To test this hypothesis, we analyzed the FAs at the sn-2 position of the individual galactolipids. There was a significant increase in the relative proportion of C18 FAs at the sn-2 position of both MGDG and DGDG in the double mutants relative to tgd1-1, indicating an increased eukaryotic pathway activity for galactolipid synthesis in the double mutants. Because the tgd1-1 mutant carries a leaky point mutation in a permease-like protein involved in ER-to-plastid lipid import, the increased eukaryotic pathway of galactolipid synthesis may be attributable to the increased availability of lipid substrates for the TGD1-associated lipid transfer system due to blocked FA turnover in the double mutants.

Overexpression of SDP1 Decreases TAG Levels in tgd1-1:

To provide additional evidence to support a role of SDP1, but not other lipase candidates in TAG hydrolysis in leaves, we generated transgenic plants overexpressing SDP1, SDP1L, CGI58L or ATGL from the constitutive 35S promoter in the tgd1-1 background. Multiple independent transgenic lines for each construct were tested for leaf TAG content by thin layer chromatography (TLC). Five representative lines for each transgene were selected for detailed analysis. Overexpression of SDP1, but not other candidate lipases, significantly decreased leaf TAG content in tgd1-1. The average leaf TAG content in 5-week-old plants grown on soil decreased by 51% in tgd1-1 overexpressing SDP1 compared with tgd1-1. In contrast, no decreases in TAG levels were noted in tgd1-1 overexpressing SDP1L, CGI58L or ATGL.

Taken together, the results from our genetic analyses are consistent with previous data (Kelly et al., 2013), showing SDP1 as a major player in TAG mobilization in vegetative tissues, while ruling out significant contributions to TAG breakdown by SDP1L, CGI-58L and ATGL.

PAH1 and PAH2 are Required for TAG Synthesis and FA Turnover in Leaves:

The Arabidopsis genome harbors two highly similar lipin homolog genes encoding $Mg^{2+}$-dependent PAHs that function redundantly in catalyzing the dephosphorylation of PA to DAG (Nakamura et al., 2009; Eastmond et al., 2010), the direct precursor of TAG and phospholipid synthesis. To test their role in TAG synthesis and FA degradation in leaves, we constructed a double mutant lacking PAH1 and PAH2 by genetic crossing. This double mutant is the same allele combination as that described previously by Nakamura et al. (2009) and Eastmond et al. (2010) and was designated as pah1 pah2-1 by Eastmond et al. (2010). Genetic crosses were made between pah1 pah2-1 and tgd1-1 or PDAT1 overexpressing line 3. The tgd1-1 pah1 pah2-1 triple mutant and the PDAT1 overexpressing line in the pah1 pah2-1 background were subsequently recovered. The amount of TAG in leaves of tgd1-1 pah1 pah2-1 was decreased by 66% compared with tgd1-1. In the PDAT1 overexpressing line 3, disruption of two PAH genes resulted in an 83% reduction in leaf TAG content, relative to the transgenic lines in the wild-type background. There was also a moderate (38%) but significant (P=0.05, n=3) reduction in TAG level in leaves of the pah1 pah2-1 double mutant relative to the wild type. These results suggest that, in contrast to seeds (Eastmond et al., 2010), PA dephosphorylation catalyzed by PAH1 and PAH2 is the major source of DAG for TAG synthesis in leaves.

We next compared the rate of the decay in labeled FAs following a pulse of $^{14}C$-acetate applied to excised leaves. During the 1 h of pulse, there was no significant (P=0.32, n=3) difference in amounts of label incorporation into total FAs between the wild type (3.67±0.25 K disintegrations per minute (KDPM)/mg FW) and the pah1 pah2-1 double mutant (3.76±0.07 KDPM/mg FW). During the 3 day chase, the total label decreased by 13.9% to 3.16±0.11 KDPM/mg FW (n=3) in the wild type, corresponding to an average decay rate of 4.6% per day. Remarkably, the amount of labeled FAs stayed almost unaltered in the pah1 pah2-1 double mutant (3.64±0.15 KDPM/mg FW, n=3) during the same chase period. These results suggest a role of PAH1 and PAH2 in the regulation of FA turnover in leaves.

Plant Materials and Growth Conditions:

The Arabidopsis (Arabidopsis thaliana) plants used in this study were of the Columbia ecotype. The tgd1 mutant was previously described by Xu et al., 2003; act1 by Kunst et al., 1988, and the transgenic lines overexpressing PDAT1 by Fan et al., 2013b. The T-DNA insertion mutants for PXA1 (SALK_019334, pxa1-2, Kunz et al., 2009), SDP1 (SALK_102887, sdp1-4, Eastmond, 2006), SDP1L (SALK_119557, sdp1L, Kelly et al., 2011), ATGL (SALK_139011, atgL, Kelly et al., 2011), PAH1 (SALK_042850, pah1, Nakamura et al., 2009) and PAH2 (SALK_047457, pah2-1, Eastmond et al., 2010) were obtained from the ABRC at Ohio State University (Alonso, 2003). The homozygosity of the T-DNA lines were verified by PCR. The mutant line with a T-DNA insertion in CGI58L (cgi58L) was kindly provided by Kent Chapman.

For growth on plates, surface-sterilized seeds of Arabidopsis were germinated on 0.6% (w/v) agar-solidified half-strength Murashige and Skoog (MS) (Murashige and Skoog, 1962) medium supplemented with 1% (w/v) sucrose in an incubator with a photon flux density of 80-120 µmol $m^{-2}$ $s^{-1}$ and a light period of 16 h (22° C.) and a dark period of 8 h (18° C.). For growth on soil, plants were first grown on MS medium for 10 days and then transferred to soil and grown under a photosynthetic photon flux density of 150-200 µmol $m^{-2}$ $sec^{-1}$ at 22/18° C. (day/night) with a 16 h light/8 h dark period.

Generation of Plant Expression Vectors and Plant Transformation:

The full-length coding regions of SDP1, SDP1L, CGI58L and ATGL were amplified by RT-PCR. The resulting PCR products were restricted with XmaI/SalI, SacI/KpnI, PstI/KpnI or XbaI/KpnI, respectively and inserted into the respective sites of binary vectors derived from pPZP212 (Hajdukiewicz et al., 1994). After confirming the integrity of the constructs by sequencing, plant stable transformation was performed according to Clough and Bent, 1998. Transgenic plants were selected in the presence of the respective antibiotics for the vectors on MS medium.

Lipid and Fatty Acid Analyses:

Plant tissues were frozen in liquid nitrogen and total lipids were extracted by homogenization in chloroform/methanol/formic acid (1:1:0.1, by volume) and 1 M KCl-0.2 M $H_3PO_4$ according to Dörmann et al., 1995. Neutral and total polar lipids were separated on silica plates (Si250 with preadsorbant layer; Mallinckrodt Baker) by thin layer chromatography using a solvent system of hexane-diethyl ether-acetic acid (70:30:1, by volume). Polar lipids were separated using a solvent system consisting of acetone/toluene/water (91:30:7, by volume). Lipids were visualized by spraying 5% $H_2SO_4$ followed by charring. For quantitative analysis, lipids were visualized by brief exposure to iodine vapor and identified by co-chromatography with lipid standards. Individual lipids were scraped from the plate and used to prepare fatty acid methyl esters. Separation and identification of the fatty acid methyl esters (FAMEs) was performed on an HP5975 gas chromatography-mass spectrometer (Hewlett-Packard, Palo Alto, Calif.) fitted with 60 m×250 µm SP-2340 capillary column (Supelco, Bellefonte, Pa.) with helium as a carrier gas. The methyl esters were quantified using heptadecanoic acid as the internal standard as described by Fan et al. (2011). The TAG content was calculated according to Li et al. (2006). The fatty acid composition at the sn-2 position of the glycerol backbone was determined by *Rhizopus arrhizus* lipase digestion as described in Härtel et al., 2000.

Acetate Labeling:

In vivo labeling experiments with $^{14}C$-acetate were done according to Koo et al., 2005. Briefly, rapidly growing leaves of 7-week-old plants were cut in strips and then incubated in the light (60 µmol $m^{-2}$ $s^{-1}$ at 22° C. with shaking in 10 ml of medium containing 1 mM unlabeled acetate, 20 mM MES pH5.5, one-tenth strength of MS salts and 0.01% Tween 20. The assay was started by the addition of 0.1 mCi of $^{14}C$-acetate (106 mCi/mmol; American Radiolabeled Chemicals, St. Louis). At the end of incubation, leaf strips were washed three times with water and blotted onto filter paper. For the chase period, leaf tissue was incubated in the same medium lacking $^{14}C$-acetate under the same conditions as used for the pulse. Total lipids were extracted and separated as described above and radioactivity associated with total lipids or different lipid classes was determined by liquid scintillation counting.

OD Imaging:

For OD imaging, leaf tissues were stained with a neutral lipid specific fluorescent dye, Nile red (Sigma-Aldrich) at a final concentration of 50 µg/mL, and observed under a Zeiss epifluorescence microscope (Carl Zeiss, Axiovert 200M, Germany) with a green fluorescent protein filter. For transmission electron microscopy, leaf tissues were fixed with 2.5% (v/v) glutaraldehyde in 0.1 M sodium cacodylate buffer (pH 7.4) for 2 h, and then post-fixed with 1% osmium tetroxide in the same buffer for 2 h at room temperature. After dehydration in a graded series of ethanol, the tissues were embedded in EPON812 resin (Electron Microscopy Sciences, Hatfield, Pa., USA), sectioned and stained with 2% uranyl acetate and lead citrate before viewing under a JEOL JEM-1400 LaB6 120 KeV transmission electron microscope (JEOL Inc., Peabody, Mass., USA).

REFERENCES

Adeyo, O., Horn, P. J., Lee, S. K., Binns, D. D., Chandrahas, A., Chapman, K. D., and Goodman, J. M. (2011) J. Cell Biol. 192:1043-1055.

Alonso, J. M. (2003) Science 301:1849-1849.

Bagnato, C. and Igal, R. A. (2003) J. Biol. Chem. 278: 52203-52211.

Bao, X., Focke, M., Pollard, M., and Ohlrogge, J. (2000) Plant J. 22:39-50.

Bonaventure, G., Ba, X. M., Ohlrogge, J., and Pollard, M. (2004) Plant Physiol. 135:1269-1279.

Browse, J., Kunst, L., Anderson, S., Hugly, S., and Somerville, C. (1989) Plant Physiol. 90:522-529.

Caviglia, J. M., De Gomez Dumm, I. N., Coleman, R. A., and Igal, R. A. (2004) J. Lipid Res. 45:1500-1509.

Chapman, K. D., and Ohlrogge, J. B. (2012) J. Biol. Chem. 287:2288-2294.

Clough, S. J., and Bent, A. F. (1998) The Plant J. 16:735-743.

De Marcos Lousa, C., van Roermund, C. W., Postis, V. L., Dietrich, D., Kerr, I. D., Wanders, R. J., Baldwin, S. A., Baker, A., and Theodoulou, F. L. (2013) Proc. Natl. Acad. Sci. USA 110:1279-1284.

Dörmann, P., Hoffmann-Benning, S., Balbo, I., and Benning, C. (1995) The Plant Cell 7:1801-1810.

Eastmond, P. J. (2006) The Plant Cell 18:665-675.

Eastmond, P. J., Quettier, A. L., Kroon, J. T. M., Craddock, C., Adams, N., and Slabas, A. R. (2010) The Plant Cell 22:4216-4216.

Fakas, S., Qiu, Y. X., Dixon, J. L., Han, G. S., Ruggles, K. V., Garbarino, J., Sturley, S. L., and Carman, G. M. (2011) J. Biol. Chem. 286:29074-29085.

Fan, J., Andre, C., and Xu, C. (2011) FEBS Lett. 585:1985-1991.

Fan, J. L., Yan, C. S., and Xu, C. C. (2013a) The Plant J. 76:930-942.

Fan, J. L., Yan, C. S., Zhang, X. B., and Xu, C. C. (2013b) The Plant Cell 25:3506-3518.

Gaspar, M. L., Jesch, S. A., Viswanatha, R., Antosh, A. L., Brown, W. J., Kohlwein, S. D., and Henry, S. A. (2008) J. Biol. Chem. 283:25735-25751.

Ghosh, A. K., Chauhan, N., Rajakumari, S., Daum, G., and Rajasekharan, R. (2009) Plant Physiol. 151:869-881.

Golden, A., Liu, J., and Cohen-Fix, 0. (2009) J. Cell Sci. 122:1970-1978.

Graham, I. A. (2008) Ann. Rev. Plant Biol. 59:115-142.

Hajdukiewicz, P., Svab, Z., and Maliga, P. (1994) Plant Mol. Biol. 25:989-994.

Härtel, H., Dormann, P., and Benning, C. (2000) Proc. Natl. Acad. Sci. USA 97:10649-10654.

Henry, S. A., Kohlwein, S. D., and Carman, G. M. (2012) Genetics 190:317-349. Hermansson, M., Hokynar, K., and Somerharju, P. (2011) Prog. Lipid Res. 50:240-257.

Holthuis, J. C., and Menon, A. K. (2014) Nature 510:48-57.

Igal, R. A., and Coleman, R. A. (1996) J. Biol. Chem. 271:16644-16651.

James, C. N., Horn, P. J., Case, C. R., Gidda, S. K., Zhang, D. Y., Mullen, R. T., Dyer, J. M., Anderson, R. G. W., and Chapman, K. D. (2010) Proc. Natl. Acad. Sci. USA 107:17833-17838.

Kelly, A. A., Quettier, A. L., Shaw, E., and Eastmond, P. J. (2011) Plant Physiol. 157:866-875.

Kelly, A. A., van Erp, H., Quettier, A. L., Shaw, E., Menard, G., Kurup, S., and Eastmond, P. J. (2013) Plant Physiol. 162:1282-1289.

Kobayashi, K., Kondo, M., Fukuda, H., Nishimura, M., and Ohta, H. (2007) Proc. Natl. Acad. Sci. USA 104:17216-17221.

Kohlwein, S. D., Veenhuis, M., and van der Klei, I. J. (2013) Genetics 193:1-50. Koo, A. J. K., Fulda, M., Browse, J., and Ohlrogge, J. B. (2005) The Plant J. 44:620-632.

Kunst, L., Browse, J., and Somerville, C. (1988) Proc. Natl. Acad. Sci. USA 85:4143-4147.

Kunz, H. H., Scharnewski, M., Feussner, K., Feussner, I., Flugge, U. I., Fulda, A., and Gierth, M. (2009) The Plant Cell 21:2733-2749.

Leonardi, R., Frank, M. W., Jackson, P. D., Rock, C. O., and Jackowski, S. (2009) J. Biol. Chem. 284:27077-27089.

Malanovic, N., Streith, I., Wolinski, H., Rechberger, G., Kohlwein, S. D., and Tehlivets, 0. (2008) J. Biol. Chem. 283:23989-23999.

Murashige, T., and Skoog, F. (1962) Physiol. Plant 15:473-497.

Nakamura, Y., Koizumi, R., Shui, G., Shimojima, M., Wenk, M. R., Ito, T., and Ohta, H. (2009) Proc. Natl. Acad. Sci. USA 106:20978-20983.

Nohturfft, A., and Zhang, S. C. (2009) Ann. Rev. Cell Dev. Biol. 25:539-566.

Ohlrogge, J., and Browse, J. (1995) The Plant Cell 7:957-970.

Park, S., Gidda, S. K., James, C. N., Horn, P. J., Khuu, N., Seay, D. C., Keereetaweep, J., Chapman, K. D., Mullen, R. T., and Dyer, J. M. (2013) The Plant Cell 25:1726-1739.

Petschnigg, J., Wolinski, H., Kolb, D., Zellnig, G., Kurat, C. F., Natter, K., and Kohlwein, S. D. (2009) J. Biol. Chem. 284:30981-30993.

Santos-Rosa, H., Leung, J., Grimsey, N., Peak-Chew, S., and Siniossoglou, S. (2005) EMBO J. 24:1931-1941.

Slocombe, S. P., Cornah, J., Pinfield-Wells, H., Soady, K., Zhang, Q., Gilday, A., Dyer, J. M., and Graham, I. A. (2009) Plant Biotechnology J. 7:694-703.

Theodoulou, F. L., and Eastmond, P. J. (2012) Curr. Opin. in Plant Biol. 15:322-328.

van Meer, G., Voelker, D. R., and Feigenson, G. W. (2008) Nat. Rev. Mol. Cell Biol. 9:112-124.

Xu, C., Fan, J., Cornish, A. J., and Benning, C. (2008) The Plant Cell 20:2190-2204.

Xu, C., Fan, J., Riekhof, W., Froehlich, J. E., and Benning, C. (2003) EMBO J 22:2370-2379.

Xu, C., Fan, J., Froehlich, J. E., Awai, K., and Benning, C. (2005) The Plant Cell 17:3094-3110.

The invention claimed is:

1. A plant comprising a plant vegetative tissue comprising five percent or more of dry weight triacylglycerol (TAG) compounds wherein the plant is *Arabidopsis thaliana, Beta vulgaris, Brassica napus, miscanthus, camellina*, switchgrass, corn, sugarcane, sorghum, *Sacharum spontaneum*, soybean, sunflower, cotton, or duckweeds which are members of the Lemnoideae; in which a gene encoding a trigalactosyldiacylglycerol (TGD) protein is mutated and either a gene encoding a sugar dependent 1 (SDP1) triacylglycerol lipase is mutated or a gene encoding a peroxisomal transporter 1 (PXA1) protein is mutated, or both, wherein said mutations substantially inactivate said encoded protein, lipase and/or transporter.

2. The plant of claim 1 wherein the plant is *Arabidopsis thaliana*.

3. The plant of claim 1 wherein the tissue is selected from the group consisting of leaves, stems and roots.

4. The plant of claim 1 wherein the tissue is stems and leaves.

5. The plant of claim 1 wherein the tissue is leaves.

6. A plant comprising a plant vegetative tissue having five percent or more of dry weight triacylglycerol (TAG) compounds and a defective trigalactosyldiacylglycerol 1 (TGD 1) protein and either a defective sugar dependent triacylglycerol lipase (SDP1) or a defective peroxisomal transporter 1 (PXA1) protein, or both wherein the plant is *Arabidopsis thaliana, Beta vulgaris, Brassica napus, miscanthus, camellina*, switchgrass, corn, sugarcane, sorghum, *Sacharum spontaneum*, soybean, sunflower, cotton, or duckweeds which are members of the Lemnoideae.

7. A plant comprising a plant vegetative tissue having five percent or more of dry weight triacylglycerol (TAG) compounds and a defective gene encoding a substantially an inactive TGD1 protein and either a defective gene encoding a defective SDP1 lipase or a defective PXA1 protein, or both wherein the plant is *Arabidopsis thaliana, Beta vulgaris, Brassica napus, miscanthus, camellina*, switchgrass, corn, sugarcane, sorghum, *Sacharum spontaneum*, soybean, sunflower, cotton, or duckweeds which are members of the Lemnoideae.

8. The plant of claim 7 wherein the defective gene encoding the inactive TGD1 protein is tgd 1-1.

9. The plant of claim 7 wherein said defective genes are created by mutation, DNA insertion, DNA deletion, or by knockout.

10. A plant comprising a plant vegetative tissue having five percent or more of dry weight triacylglycerol (TAG) compounds and substantially suppressed TGD1 protein activity and either a substantially suppressed SDP1 lipase activity or a substantially suppressed PXA1 transporter activity, or both wherein the plant is *Arabidopsis thaliana, Beta vulgaris, Brassica napus, miscanthus, camellina*, switchgrass, corn, sugarcane, sorghum, *Sacharum spontaneum*, soybean, sunflower, cotton, or duckweeds which are members of the Lemnoideae.

11. The plant of claim 10 wherein suppressed activity of one or more of said protein, lipase or transporter is the result of introduction of one or more inhibitory RNA sequences.

12. A plant comprising a plant vegetative tissue having five percent or more of dry weight triacylglycerol (TAG) compounds and mutant plant cells in which TGD1 protein and either SDP1 or PXA1 protein, or both, are substantially inactive wherein the plant is *Arabidopsis thaliana, Beta vulgaris, Brassica napus, miscanthus, camellina*, switchgrass, corn, sugarcane, sorghum, *Sacharum spontaneum*, soybean, sunflower, cotton, or duckweeds which are members of the Lemnoideae.

13. The plant of claim 12 wherein the plant is *Arabidopsis thaliana*.

14. The plant of claim 6 wherein activity of TGD1 and either or both SDP1 and PXA1 protein is less than 50% of the activity of wild type plant cells.

15. The plant of claim 14 wherein activity of TGD1 protein and either or both SDP1 and PXA1 protein is less than 70% of the activity of wild type plant cells.

16. The plant of claim 15 wherein activity of TGD1 protein and either or both SDP1 and PXA1 protein is less than 90% of the activity of wild type plant cells.

* * * * *